United States Patent [19]

Rabine et al.

[11] Patent Number: 4,582,425

[45] Date of Patent: Apr. 15, 1986

[54] DEVICE FOR PREPARING COLORIMETER SAMPLE

[75] Inventors: Bruce A. Rabine, Oakdale; Steven M. Stensvad, White Bear Lake Township, Ramsey County, both of Minn.

[73] Assignee: Minnesota Mining and Manufacturing Company, St. Paul, Minn.

[21] Appl. No.: 637,487

[22] Filed: Aug. 3, 1984

[51] Int. Cl.$^4$ ............................ G01N 1/28; G01N 21/01
[52] U.S. Cl. ........................................ 356/36; 356/244
[58] Field of Search ................... 356/36, 38, 244, 402, 356/445

[56] References Cited

U.S. PATENT DOCUMENTS 3,232,711  2/1966  Senyk et al. ................ 356/38 X
3,614,230  10/1971  Crawford ................... 356/36

Primary Examiner—Vincent P. McGraw
Attorney, Agent, or Firm—D. M. Sell; J. A. Smith; D. B. Little

[57] ABSTRACT

The novel device prepares samples of loose particles such as roofing granules to present a level surface from which colorimeter measurements can be made. The particles to be measured overfill a dish, the lip of which has a bevel providing a knife edge at its inner diameter. A roller is rolled back and forth across the dish to push excess particles beyond the knife edge from which they fall through a grid on which the dish rests.

11 Claims, 1 Drawing Figure

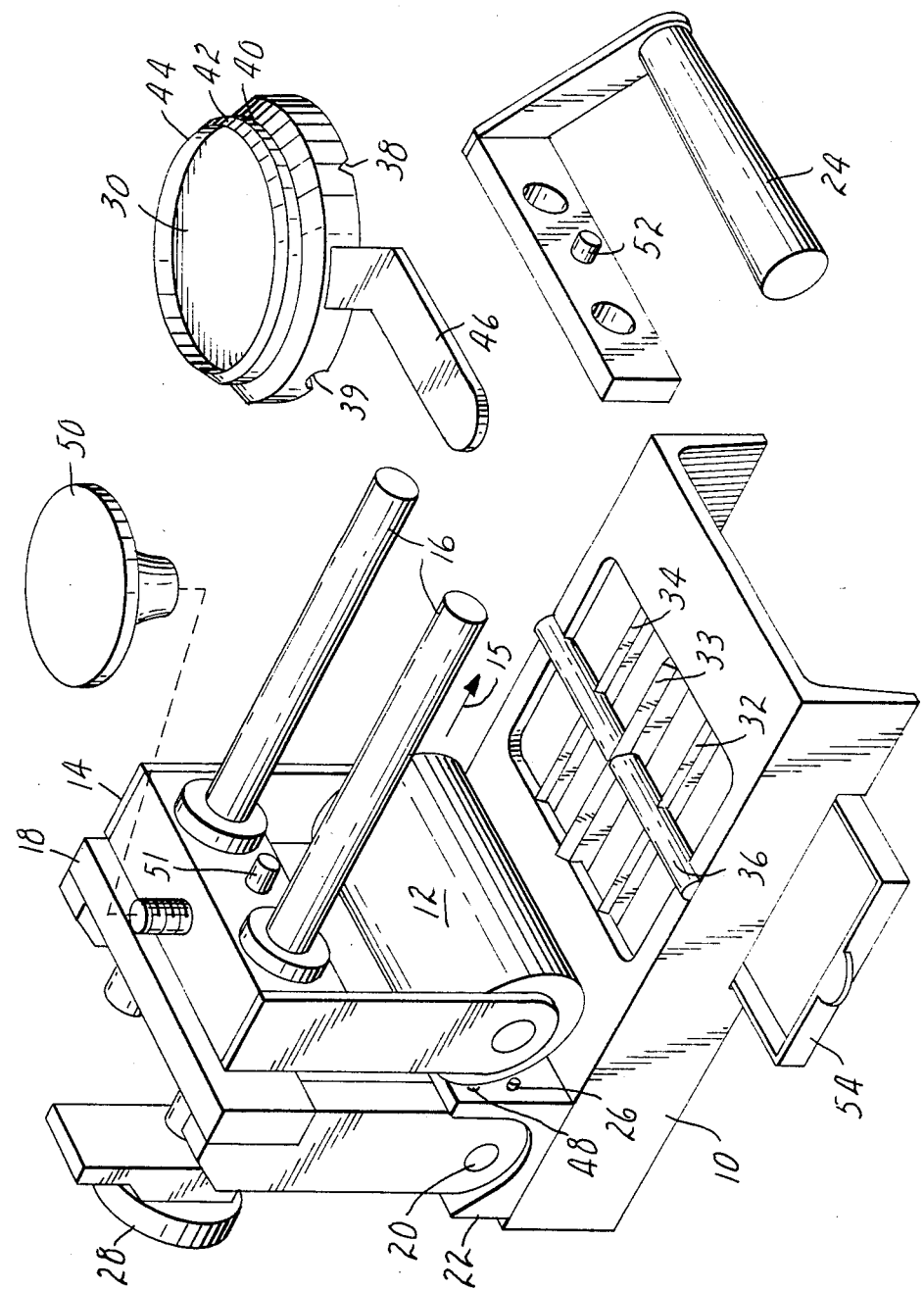

DEVICE FOR PREPARING COLORIMETER SAMPLE

FIELD OF THE INVENTION

The invention concerns a mechanical device for preparing samples of loose particles such as roofing granules to present a level surface from which colorimeter measurements can be made accurately and reproducibly.

BACKGROUND ART

Roofing granules are coated with opaque pigments in order to shield asphaltic roofing materials from ultraviolet radiation and also to provide an esthetically pleasing appearance. Because pigments tend to be much more expensive than the starting granules, it is important to keep the pigment proportion to the minimum that will provide both the desired ultraviolet protection and esthetic appearance. It is even more important to maintain uniformity of color from batch to batch produced over prolonged periods of time. Accordingly, colorimeter tests are periodically performed while pigmenting the granules. When the granules are being coated with a mixture of pigments, the proportion of each pigment must be carefully controlled and verified by periodic testing to achieve the desired coloration.

In the prior art, colorimeter samples have been prepared by overfilling a dish with a mass of loose roofing granules and flattening the surface of the mass with a flat object. Only operators of considerable skill and experience are able to obtain a surface uniformity providing reasonably uniform colorimeter measurements.

The same problem of obtaining reproducible colorimeter measurements has been encountered in the production of other types of loose particles, for example, the pigments themselves, which either may be dry or dispersed in a liquid when being checked for color. Among other types of loose particles which need to be checked for color uniformity are colored glass beads.

DISCLOSURE OF INVENTION

The present invention concerns a mechanical device for arranging a mass of loose particles to present a uniformly level surface, thus enabling the color of the particles to be reproducibly measured. The novel mechanical device comprises a dish having an annular lip which has a bevel providing a knife edge at the inner diameter of the lip, and
a base comprising
a cylindrical roller, the axial width of which exceeds the diameter of the lip of the dish,
a carriage for moving the roller horizontally in a direction transversely to its axis,
a dish support for holding the dish rigidly in the direction of roller travel, and
said carriage including means for moving the roller to roll completely across the knife edge of the dish so that when the dish has been overfilled with loose particles, a level particle surface results.

A preferred device of the invention includes a linear bearing carriage comprising two parallel shafts with adjustable stops to restrict the travel of the roller to a precise path and distance slightly exceeding the diameter of the lip of the dish. The shafts are rigidly held in cantilever fashion by a yoke which pivots at the base, both to allow the carriage to be raised for unobstructed positioning and removal of the dish and to allow the roller to ride up slightly when moved onto the lip of the dish, with the full weight of the roller and much of the weight of the carriage bearing against the lip.

In the preferred device, the dish support comprises a grid including a central rail having a knife edge extending in the longitudinal direction. The underside of the dish is formed with a V-shaped channel, the apex of which rests on the knife edge. The angle of the channel may slightly exceed that of the rails' knife edge to allow the dish to pivot slightly in the transverse direction until stopped by lateral portions of the grid.

Because roofing granules are highly abrasive, both the dish and the roller are preferably hardened steel, both having a Rockwell C hardness from about 53 to about 58. Above about 58 would entail brittleness and a sharpening problem. Below about 53 would entail undue edge wear unless the particles being measured were less abrasive than are ordinary roofing granules.

The bevel of the lip of the dish is preferably between 20° and 50° to the horizontal when the dish is positioned on the dish support. At more than 50°, the knife edge would be prone to damage, and at less than 20°, the roller might not clear the lip of particles, especially particles which are unusually small and have sharp edges.

The depth of the dish should be at least twice (preferably at least 5 times) the maximum diameter of an average particle and greater than the maximum diameter of every particle. Preferably the diameter of the knife edge is substantially greater than the field of view of the colorimeter since any unevenness in the surface of the sample is likely to be near the edge of the dish after the roller has passed back and forth across the dish.

The dish preferably is fitted with a handle to facilitate lifting it from the rails and placing it onto a colorimeter stage without disturbing any of the particles. The carriage preferably has two handles, one at its free extremity for pivoting it between its working and dish-access positions, and another immediately above and affixed to the roller for moving the roller across a particle-filled dish.

THE DRAWING

In the drwing the single FIGURE is an exploded schematic perspective view of a device embodying the invention.

The device of the drawing, which is shown in its working position, comprises a base 10 and a cylindrical roller 12 affixed to a linear bearing carriage 14 along which the roller can move horizontally back and forth in the longitudinal direction indicated by the arrow 15. The carriage includes two parallel shafts 16 which are rigidly cantilevered from a yoke 18. The yoke pivots on a shaft 20 which is journalled in a bracket 22 that is rigidly affixed to the base 10. Fixed to the outer ends of the shafts 16 is a handle 24 by which an operator can raise the carriage 14 to an angle of approximately 45°, at which point a spring-loaded ball and detent 26 in the bracket 22 fits into a shallow depression (not shown) in the yoke 18. The ball and detent 26, together with a counterweight 28, hold the carriage safely in the raised position until the operator forces it downwardly to the working position shown in the drawing.

While the carriage is pivoted upwardly, the operator places an overfilled sample dish 30 onto a grid comprising three rails 32, 33 and 34 plus a cylindrical locator rod 36. Each of the rails has a knife edge, thus insuring that any loose particles drop through the grid. The underside of the sample dish 30 is formed with a V-shaped channel 38, the apex of which rests on the knife edge of the central rail 33 when the dish is in the operating position. The angle formed by the V-shaped channel 38 is a fraction of a degree greater than that of the rail 33 at its knife edge, thus permitting the dish to pivot slightly in the transverse direction until stopped by the side rails 32, 34 and the locator rod 36 which fits into a semicylindrical channel 39 in the underside of the dish 30. When the knife edge of the dish 30 is precisely horizontal, the semicylindrical channel 39 of the dish does not contact the cylindrical rod 36 which, as do the side rails 32 and 34, serves as a stop to prevent the roller 12 from forcing the dish 30 out of an essentially horizontal attitude.

The dish 30 has an annular lip 40 which has a bevel 42 providing a circular knife edge 44 at the inner diameter of the lip. An angular handle 46 is screwed to the dish 30 in the position shown for a right-handed operator who normally would lift the dish with the left hand while retracting the spring-loaded dish-retainer of the colorimeter with the right hand. The handle 46 can be reversed for a left-handed operator.

When the carriage 14 is lowered to the working position as shown, its downward movement is stopped by a screw 48 which is adjustable so that the roller 12 contacts the bevel 42 of the lip 40 of the dish 30. The operator then grasps a handle 50 and moves the roller 12 in the direction of the arrow 15. This movement slightly raises the rollr so that its full weight and part of the weight of the carriage 14 bear against the knife edge 44. The roller 12 is moved completely across the knife edge 44 and begins to roll down the bevel 42 until a stop 51 strikes an adjustable spring plunger 52. The operator moves it back to the illustrated position before pivoting the carriage 14 upwardly to remove the dish 30. Each time the roller 12 moves across the dish, it pushes excess particles beyond the knife edge 44 from which they fall between the rails 32, 33 and 34 and the locator rod 36 to be collected in a slidable pan 54.

EXAMPLE

The device shown in the drawing has been constructed entirely of steel except for plastic handles 24 and 50 and bronze bushings for the shaft 20. Significant details of the device are:
Roller 12 diameter—5.08 cm
   transverse width—8.89 cm
Shafts 16 diameter—1.91 cm
Cylindrical Locator Rod 36 diameter—1.27 cm
Rail edge angle for Rails 32, 33 & 34—90°
Lip 40 thickness—0.15 cm
   inner diameter—7.30 cm
   depth at knife edge 44—0.48 cm
Bevel 42 angle from horizontal—30°

Before construction of the device of the Example, (below called "Device II"), a similar device had been constructed (below called "Device I") which was the same as Device II except that the steel of its dish and its roller had not ben hardened, and the dish was held on a flat plate having three pins which fit into holes drilled into the underside of the dish. Device I was used to prepare colorimeter samples of roofing granules having a maximum diameter of 1.65 mm. In doing so, its dish was overfilled, and the roller was drawn twice across the dish and returned to the starting position before removal of the dish. Results of testng with a "Hunter Labscan" colorimeter are reported in Tables A-C in comparison to a prior art technique wherein a flat object was used to provide a flat surface of granules in a stamped-metal dish having a seamless cylinrical lip 0.40 mm in thickness and 6.1 cm in diameter. The testing was carried out by eight operators, each of whom prepared three samples of each of two batches of roofing granules, one white and one brown, using Device I and then made L*, a* and b* measurements of each sample. The same sequence also carried out by each operator using the prior art techinque.

TABLE A (L* Measurements)

| | Device I | Prior Art |
|---|---|---|
| Averages: | | |
| Range of means (between operators) | 0.24 | 0.74 |
| Variance between operators | 0.0077 | 0.0546 |
| Variance within an operator | 0.0091 | 0.0631 |

TABLE B (a* Measurements)

| | Device I | Prior Art |
|---|---|---|
| Averages: | | |
| Range of mean (between operators) | 0.09 | 0.09 |
| Variance between operators | 0.0004 | 0.0001 |
| Variance within an operator | 0.0009 | 0.0006 |

TABLE C (b* Measurements)

| | Device I | Prior Art |
|---|---|---|
| Averages: | | |
| Range of means (between operators) | 0.16 | 0.19 |
| Variance between operators | 0.0023 | 0.0005 |
| Variance within an operator | 0.0042 | 0.0069 |

All measurements were made in CIE L* a* b* units, L* indicating lightness/darkness, a* indicating redness/greenness, and b* indicating yellowness/blueness. Device I significantly improved the reliability of L* measurements as compared to the prior art technique. There was no significant difference in the reliability of a* and b* measurements when using either Device I or the prior art technique.

After Device II was built, it was tested in comparison to Device I. The two performed equally in making L*, a* and b* measurements.

We claim:

1. Device for arranging a mass of loose particles to present a uniformly level surface, thus enabling the color of the particles to be reproducibly measured, said device comprising
   a dish having an annular lip which has a bevel providing a knife edge at the inner diameter of the lip, and
   a base comprising
      a cylindrical roller, the axial width of which exceeds the diameter of the lip of the dish,
      a carriage for moving the roller horizontially in a direction transversely to its axis, a dish support for holding the dish rigidly in the direction of roller travel, and said carriage including means for moving the roller to roll completely across the knife edge of the dish so that when the dish has been overfilled with loose particles, a level particle surface results.

2. Device as defined in claim 1 wherein the carriage comprises two parallel shafts held in cantilever fashion by a yoke which pivots at the base to allow the carriage to be raised for unobstructed positioning and removal of the dish.

3. Device as defined in claim 2 including means for adjusting the position of the roller to contact the bevel of the dish when moved downwardly to the working position.

4. Device as defined in claim 1 wherein the bevel of the lip of the dish is between 20° and 50° to the horizontal when the dish is positioned on the dish support.

5. Device as defined in claim 4 wherein the depth of the dish is at least twice the maximum diameter of an average particle and greater than the maximum diameter of every particle to be tested.

6. Device as defined in claim 1 wherein each of the dish and roller is steel having a Rockwell C hardness from 53 to 58.

7. Device as defined in claim 1 wherein the dish support includes a central rail extending in the direction of roller travel, and the underside of the dish is formed to fit on that rail.

8. Device as defined in claim 7 wherein said central rail has a knife edge, and the underside of the dish is formed with a V-shaped channel, the apex of which rests on the knife edge.

9. Device and defined in claim 8 wherein the angle of said channel slightly exceeds that of the rail's knife edge to allow the dish to pivot transversely while the knife edge and the V of the channel remain in contact.

10. Device as defined in claim 9 wherein the angle of the rail's knife edge is about 90°.

11. Device as defined in claim 10 wherein the dish support includes a locator rod extending transversely to the rail, and the underside of the dish does not contact the locator rod when the lip of the dish is precisely horizontal.

* * * * *